US009539056B2

(12) United States Patent
Beeckler et al.

(10) Patent No.: US 9,539,056 B2
(45) Date of Patent: Jan. 10, 2017

(54) CATHETER WITH MULTIPLE IRRIGATED ELECTRODES AND A FORCE SENSOR

(71) Applicant: BIOSENSE WEBSTER (ISRAEL) LTD., Yokneam (IL)

(72) Inventors: Christopher Thomas Beeckler, Brea, CA (US); Assaf Govari, Haifa (IL); Rowan Olund Hettel, Pasadena, CA (US)

(73) Assignee: Biosense Webster (Israel) Ltd. (IL)

( * ) Notice: Subject to any disclaimer, the term of this patent is extended or adjusted under 35 U.S.C. 154(b) by 0 days.

(21) Appl. No.: 14/338,018

(22) Filed: Jul. 22, 2014

(65) Prior Publication Data

US 2014/0336640 A1 Nov. 13, 2014

Related U.S. Application Data

(63) Continuation-in-part of application No. 13/424,783, filed on Mar. 20, 2012, now Pat. No. 9,050,105.

(51) Int. Cl.
*A61B 18/14* (2006.01)
*A61B 18/00* (2006.01)

(52) U.S. Cl.
CPC .. *A61B 18/1492* (2013.01); *A61B 2018/00029* (2013.01); *A61B 2018/00166* (2013.01); *A61B 2018/00351* (2013.01); *A61B 2018/00577* (2013.01); *A61B 2018/00744* (2013.01); *A61B 2018/1467* (2013.01); *A61B 2090/065* (2016.02); *A61B 2218/002* (2013.01)

(58) Field of Classification Search
CPC ............ A61B 2019/465; A61B 5/6885; A61M 2025/0002
See application file for complete search history.

(56) References Cited

U.S. PATENT DOCUMENTS

| 8,517,999 B2* | 8/2013 | Pappone et al. ............... 604/264 |
| 2008/0009750 A1 | 1/2008 | Aeby et al. |
| 2008/0275428 A1 | 11/2008 | Tegg et al. |
| 2008/0294144 A1 | 11/2008 | Leo et al. |
| 2009/0093806 A1 | 4/2009 | Govari et al. |
| 2010/0030209 A1 | 2/2010 | Govari et al. |
| 2010/0079158 A1 | 4/2010 | Bar-Tal et al. |
| 2010/0152574 A1 | 6/2010 | Erdman et al. |

(Continued)

FOREIGN PATENT DOCUMENTS

| EP | 2347726 | 7/2011 |
| EP | 2 550 924 A1 | 1/2013 |

(Continued)

OTHER PUBLICATIONS

European Search Report of corresponding European Patent Application No. 15177934.5 dated Nov. 23, 2015.

(Continued)

*Primary Examiner* — Michael Kahelin

(57) ABSTRACT

A probe, including an insertion tube and an electrode mounted on a distal end of the insertion tube. A force sensor is mounted in the distal end of the insertion tube. The force sensor has a central opening and is configured to measure a force on the distal end. The probe also includes tubing, passing through the central opening, which is configured to supply irrigation fluid through apertures in the electrode.

14 Claims, 3 Drawing Sheets

(56) References Cited

U.S. PATENT DOCUMENTS

2010/0168548 A1    7/2010   Govari et al.
2011/0130648 A1    6/2011   Beeckler et al.
2012/0071870 A1    3/2012   Salahieh et al.

FOREIGN PATENT DOCUMENTS

EP           2 641 555 A1    9/2013
EP           2 740 432 A2    6/2014
WO    WO 2011/143468 A2    11/2011

OTHER PUBLICATIONS

Chinese Office Action of corresponding Chinese Patent Application No. 2013100906064 dated Mar. 28, 2016.

\* cited by examiner

CATHETER WITH MULTIPLE IRRIGATED ELECTRODES AND A FORCE SENSOR

RELATED APPLICATIONS

This application claims the benefit of and priority to U.S. patent application Ser. No. 13/424,783, filed Mar. 20, 2012, entitled "Catheter With Multiple Irrigated Electrodes And A Force Sensor," and which is incorporated herein by reference in its entirety.

FIELD OF THE INVENTION

The present invention relates generally to catheters having electrodes, and specifically to catheters wherein the electrodes are irrigated.

BACKGROUND OF THE INVENTION

Medical procedures involving ablation of the heart may be used to cure a variety of cardiac arrhythmia, as well as to manage atrial fibrillation. Such procedures are known in the art. Other medical procedures using ablation of body tissue, such as treating varicose veins, are also known in the art. The ablation energy for these procedures may be in the form of radio-frequency (RF) energy, which is supplied to the tissue via one or more electrodes of a catheter used for the procedures.

The application of the ablation energy to body tissue, if uncontrolled, may lead to an unwanted increase of temperature of the tissue. It is consequently important to control the temperature of the tissue during any medical procedure involving ablation. One method for control is to irrigate the tissue being ablated.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

An embodiment of the present invention provides a probe, including:

an insertion tube;

an electrode mounted on a distal end of the insertion tube;

a force sensor mounted in the distal end, the force sensor having a central opening and being configured to measure a force on the distal end; and tubing, passing through the central opening, and configured to supply irrigation fluid through apertures in the electrode.

In a disclosed embodiment the electrode includes a plurality of separate electrodes having respective sets of apertures. Typically, the probe includes respective irrigation tubes, connected to the tubing, which feed the respective sets of apertures. The probe may also include a controller configured to implement respective flow rates of the irrigation fluid to the respective sets of apertures. In some embodiments the controller is configured to set at least one of the respective flow rates in response to the force on the distal end. Typically, the probe includes respective valves connected to the respective irrigation tubes, wherein the respective valves are able to set respective flow rates of the irrigation fluid to the respective sets of apertures.

In an alternative embodiment the force sensor has a tubular form enclosing a central space, and the tubing traverses the central space.

In a further alternative embodiment the force sensor includes at least one coil, and the tubing is routed through the at least one coil.

There is further provided, according to an embodiment of the present invention, a method, including:

providing an insertion tube;

mounting an electrode on a distal end of the insertion tube;

mounting a force sensor in the distal end, the force sensor having a central opening and being configured to measure a force on the distal end; and passing tubing through the central opening, the tubing being configured to supply irrigation fluid through apertures in the electrode.

A further embodiment of the present invention provides a probe, including:

an insertion tube;

a distal electrode mounted on a distal end of the insertion tube;

a force sensor mounted in the distal end, the force sensor having a central opening and being configured to measure a force on the distal end;

a proximal electrode mounted proximal to the force sensor;

first tubing, running from a proximal end of the insertion tube to the distal end, passing through the central opening, and configured to supply irrigation fluid through apertures in the distal electrode; and second tubing, running from a proximal end of the insertion tube, entering the central opening, and configured to supply irrigation fluid through apertures in the proximal electrode.

There is further provided, according to an embodiment of the present invention, a method, including:

providing an insertion tube;

mounting a distal electrode on a distal end of the insertion tube;

mounting a force sensor in the distal end, the force sensor having a central opening and being configured to measure a force on the distal end;

mounting a proximal electrode proximal to the force sensor;

passing first tubing running from a proximal end of the insertion tube through the central opening, the first tubing being configured to supply irrigation fluid through apertures in the distal electrode; and passing second tubing, running from the proximal end of the insertion tube and entering the central opening, the second tubing configured to supply irrigation fluid through apertures in the proximal electrode.

The present disclosure will be more fully understood from the following detailed description of the embodiments thereof, taken together with the drawings, in which:

DETAILED DESCRIPTION OF EMBODIMENTS

Overview

An embodiment of the present invention provides a catheter probe which is typically used for a minimally invasive procedure such as ablation of cardiac tissue. The probe comprises an insertion tube, which, in order for it to be minimally invasive, usually has a small outer diameter of approximately 2 mm. At least one electrode, and typically two or more separate electrodes, are mounted on the distal end of the insertion tube (the distal end has approximately the same diameter as the insertion tube).

Mounted within the distal end is a force sensor, which measures the force on the distal end when the end contacts tissue. (Controlling the force enables tissue ablation to be performed more precisely.) The force sensor may have a tubular form that contacts an outer sheath of the insertion tube. The sensor has a central opening, and typically defines a central space.

The one or more electrodes have respective sets of apertures, which are used to supply irrigation fluid to the electrodes and to body material in the region of the electrodes. Irrigation tubing passes through the central opening of the force sensor, typically traversing the sensor's central space, and is connected to the electrodes. The tubing supplies the irrigation fluid to the electrode apertures.

By using the "empty" region within the force sensor, i.e., the central opening and the central space, for the irrigation tubing, embodiments of the present invention use the available (small diameter) space at the distal end extremely efficiently. This efficient use of the space means that the electrodes of the distal end can be irrigated during ablation, and also that force during ablation can be measured, without requiring any increase in diameter of the catheter probe.

System Description

Figure 1:
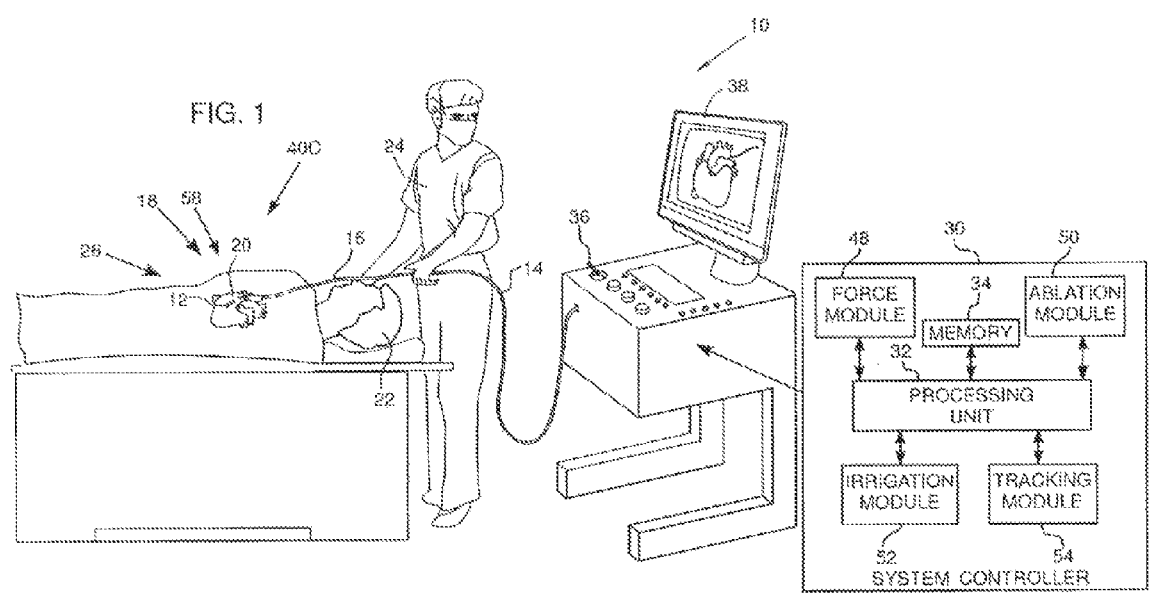
FIG. 1 is a schematic, pictorial illustration of a catheter probe ablating system, according to an embodiment of the present invention.
Figure 2:
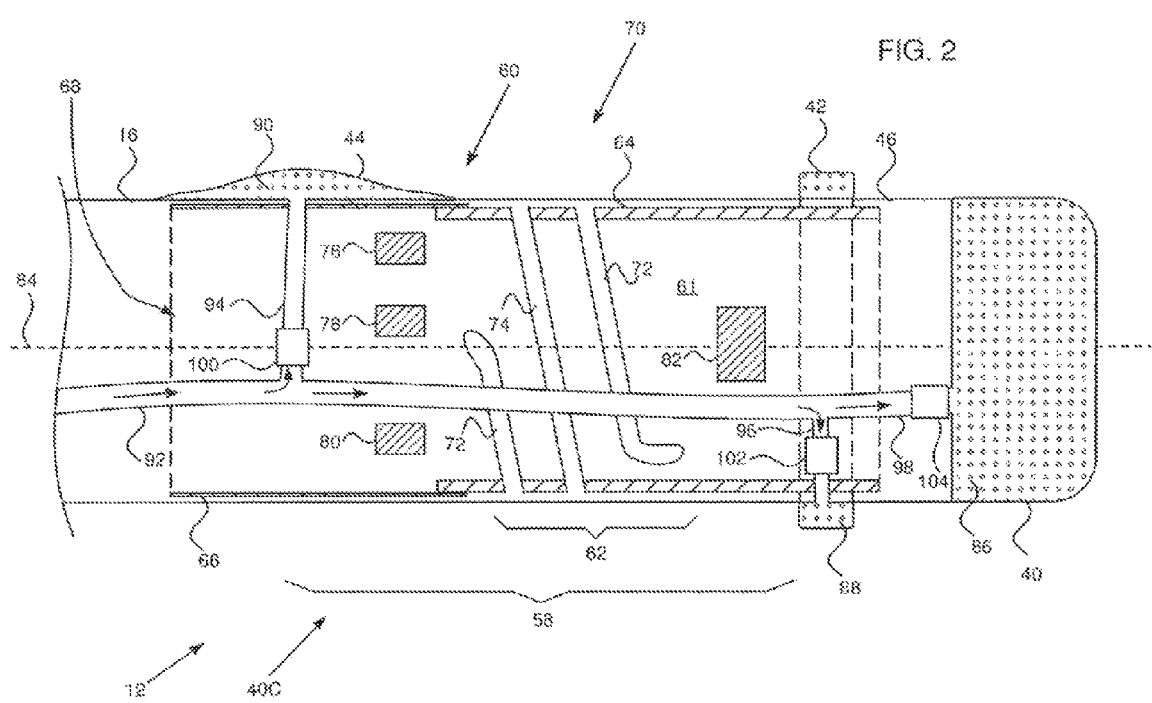
FIG. 2 is a schematic cross-section of a distal end of a catheter probe used in the system, according to an embodiment of the present invention.

Reference is now made to FIG. 1, which is a schematic, pictorial illustration of a catheter probe ablating system 10, and to FIG. 2 which is a schematic cross-section of a distal end 12 of a catheter probe 14 used in the system, according to embodiments of the present invention. In system 10, probe 14 comprises an insertion tube 16, which is inserted into a lumen 18, such as a chamber of a heart 20, of a subject 22. The probe is used by an operator 24 of system 10, during a procedure which typically includes performing ablation of body tissue 26.

For intracardiac operation, insertion tube 16 and distal end 12 should generally have a very small outer diameter, typically of the order of 2-3 mm. Therefore, all of the internal components of catheter probe 14, are also made as small and thin as possible and are arranged so as to, as much as possible, avoid damage due to small mechanical strains.

The functioning of system 10 is managed by a system controller 30, comprising a processing unit 32 communicating with a memory 34, wherein is stored software for operation of system 10. Controller 30 is typically an industry-standard personal computer comprising a general-purpose computer processing unit. However, in some embodiments, at least some of the functions of the controller are performed using custom-designed hardware and software, such as an application specific integrated circuit (ASIC) or a field programmable gate array (FPGA). Controller 30 is typically managed by operator 24 using a pointing device 36 and a graphic user interface (GUI) 38, which enable the operator to set parameters of system 10. GUI 38 typically also displays results of the procedure to the operator.

The software in memory 34 may be downloaded to the controller in electronic form, over a network, for example. Alternatively or additionally, the software may be provided on non-transitory tangible media, such as optical, magnetic, or electronic storage media.

One or more electrodes are mounted on distal end 12. By way of example, FIG. 2 illustrates three such electrodes: a first electrode 40, a second electrode 42, and a third electrode 44, the electrodes being insulated from each other. The electrodes typically comprise thin metal layers formed over an insulating sheath 46 of tube 16. Typically, the distal end has other electrodes, insulated from each other and from electrodes 40, 42, and 44, which for simplicity are not shown in the diagram. Electrode 40, at the extremity of the distal end, by way of example is assumed to have the shape of a cup with a flat base, and is herein also referred to as the cup electrode. Cup electrode 40 typically has a thickness in a range from approximately 0.1 mm to approximately 0.2 mm.

Second electrode 42 is in the form of a ring, and is also referred to herein as ring electrode 42. Ring electrode 42 is typically formed from metal having a similar thickness as the cup electrode. Third electrode 44 is in the form of protuberance or bump above sheath 46, and is also referred to as bump electrode 44. Bump electrode 44 may have a similar thickness to the cup and ring electrodes, or in some embodiments may be slightly thicker. In the present disclosure, electrodes 40, 42, and 44, and other electrodes of the distal end, are also referred to herein collectively as electrodes 40C.

Electrodes 40C are connected to system controller 30 by conductors in tube 16, not shown in the figures. As described below, at least one of the electrodes is used to ablate tissue 26. In addition to being used for ablation, the electrodes typically perform other functions, as is known in the art; some of the other functions are described below. As necessary, when used for other functions, controller 30 may differentiate between the currents for the different functions by frequency multiplexing. For example, radio-frequency (RF) ablation power may be provided at frequencies of the order of hundreds of kHz, while position sensing frequencies may be at frequencies of the order of 1 kHz. A method of evaluating the position of distal end 12 using impedances measured with respect to the electrodes is disclosed in U.S. Patent Application 2010/0079158 to Bar-Tal et al., which is incorporated herein by reference.

System controller 30 comprises a force module 48, an RF ablation module 50, an irrigation module 52, and a tracking module 54. Processing unit 32 uses the force module to generate and measure signals supplied to, and received from, a force sensor 58 in distal end 12 in order to measure the magnitude and direction of the force on the distal end. The operation and construction of force sensor 58 is described in more detail below.

Processing unit 32 uses the ablation module to monitor and control ablation parameters such as the level of ablation power applied via the one or more electrodes 40C. The module also monitors and controls the duration of the ablation that is provided.

Typically, during ablation, heat is generated in the electrode or electrodes providing the ablation, as well as in the surrounding region. In order to dissipate the heat and to improve the efficiency of the ablation process, system 10 supplies irrigation fluid to distal end 12. System 10 uses irrigation module 52 to monitor and control irrigation parameters, such as the rate of flow and the temperature of the irrigation fluid, as is described in more detail below.

Unit 32 uses tracking module 54 to monitor the location and orientation of the distal end relative to patient 22. The monitoring may be implemented by any tracking method known in the art, such as one provided in the Carto3® system produced by Biosense Webster of Diamond Bar, Calif. Such a system uses radio-frequency (RF) magnetic transmitter and receiver elements external to patient 22 and within distal end 12. Alternatively or additionally, the tracking may be implemented by measuring impedances between one or more electrodes 40C, and patch electrodes attached to the skin of patient 22, such as is also provided in the Carto3® system. For simplicity, elements specific to tracking and that are used by module 54, such as the elements and patch electrodes referred to above, are not shown in FIG. 1.

As shown in FIG. 2, distal end 12 is connected to insertion tube 16. The distal end has mounted upon it electrodes 40C, and force sensor 58 is mounted within the distal end. Aspects of a force sensor similar to force sensor 58 are described in U.S. Patent Application 2009/0093806, to Govari et al., filed Oct. 8, 2007, and in U.S. Patent Application 2011/0130648, to Beeckler et al., filed Nov. 30, 2009, both of whose disclosures are incorporated herein by reference.

FIG. 2 shows a schematic, sectional view of force sensor 58. Sensor 58 comprises a resilient coupling member 60, which forms a spring joint 62 between two ends of the coupling member. By way of example, coupling member 60 is assumed to be formed in two parts, a first part 64 and a second part 66, the two parts being fixedly joined together. The two parts of coupling member 60 are generally tubular, and are joined so that the coupling member also has a tubular form with a central opening 68. Although there is no necessity that coupling member 60 be formed of two parts, the two part implementation simplifies assembly of elements comprised in the force sensor, as well as of other elements mounted in the distal end, into the member. Typically, coupling member 60 is formed of a superelastic alloy, such as nickel titanium (Nitinol).

Coupling member 60 typically has one or more helices 70 cut in a portion of the length of first part 64 of the member, so that the member behaves as a spring. In an embodiment described herein, and illustrated in FIG. 2, helices 70 are formed as two intertwined helices, a first cut helix 72 and a second cut helix 74, which are also referred to herein as a double helix. However, coupling member 60 may have any positive integral number of helices, and those having ordinary skill in the art will be able to adapt the present description without undue experimentation to encompass numbers of helices other than two. Alternatively, the coupling member may comprise a coil spring or any other suitable sort of resilient component with similar flexibility and strength characteristics to those generated by the one or more tubular helical cuts, referred to above.

Coupling member 60 is mounted within and covered by sheath 46, which is typically formed from flexible plastic material. Member 60 typically has an outer diameter that is approximately equal to the inner diameter of sheath 46. Such a configuration, having the outer diameter of the coupling member to be as large as possible, increases the sensitivity of force sensor 58. In addition, and as explained below, the relatively large diameter of the tubular coupling member, and its relatively thin walls, provide a central space 61 enclosed within the coupling member which is used by other elements, described below, in the distal end.

When catheter probe 14 is used, for example, in ablating endocardial tissue by delivering RF electrical energy through electrodes 40C, considerable heat is generated in the area of distal end 12. For this reason, it is desirable that sheath 46 comprises a heat-resistant plastic material, such as polyurethane, whose shape and elasticity are not substantially affected by exposure to the heat.

Within force sensor 58, typically within the central space of the coupling member, a joint sensing assembly, comprising coils 76, 78, 80 and 82, provides accurate reading of any dimensional change in joint 62, including axial displacement and angular deflection of the joint. These coils are one type of magnetic transducer that may be used in embodiments of the present invention. A "magnetic transducer," in the context of the present patent application and in the claims, means a device that generates a magnetic field in response to an applied electrical current and/or outputs an electrical signal in response to an applied magnetic field. Although the embodiments described herein use coils as magnetic transducers, other types of magnetic transducers may be used in alternative embodiments, as will be apparent to those skilled in the art.

The coils in the sensing assembly are divided between two subassemblies on opposite sides of joint 62: one subassembly comprises coil 82, which is driven by a current, via a cable (not shown) from controller 30 and force module 48, to generate a magnetic field. This field is received by a second subassembly, comprising coils 76, 78 and 80, which are located in a section of the distal end that is spaced axially apart from coil 82. The term "axial," as used in the context of the present patent application and in the claims, refers to the direction of a longitudinal axis of symmetry 84 of distal end 12. An axial plane is a plane perpendicular to this longitudinal axis, and an axial section is a portion of the catheter contained between two axial planes. Coil 82 typically has an axis of symmetry generally parallel to and coincident with axis 84.

Coils 76, 78 and 80 are fixed in distal end 12 at different radial locations. (The term "radial" refers to coordinates relative to the axis 84.) Specifically, in this embodiment, coils 76, 78 and 80 are all located in the same axial plane at different azimuthal angles about the catheter axis, and have respective axes of symmetry generally parallel to axis 84. For example, the three coils may be spaced azimuthally 120° apart at the same radial distance from the axis.

Coils 76, 78 and 80 generate electrical signals in response to the magnetic field transmitted by coil 82. These signals are conveyed by a cable (not shown) to controller 30, which uses force module 48 to process the signals in order to measure the displacement of joint 62 parallel to axis 84, as well as to measure the angular deflection of the joint from the axis. From the measured displacement and deflection, controller 30 is able to evaluate, typically using a previously determined calibration table stored in force module 48, a magnitude and a direction of the force on joint 62.

Controller 30 uses tracking module 54 to measure the location and orientation of distal end 12. The method of measurement may be by any convenient process known in the art. In one embodiment, magnetic fields generated external to patient 22 create electric signals in elements in the distal end, and controller 30 uses the electric signal levels to evaluate the distal end location and orientation. Alternatively, the magnetic fields may be generated in the distal end, and the electrical signals created by the fields may be measured external to patient 22. For simplicity, the elements in distal end 12 that are used to track the distal end are not shown in FIG. 2. However, where such elements comprise coils, at least some of coils 76, 78, 80, and 82 may be used as the tracking elements required in the distal end, in addition to their use as elements of force sensor 58.

At least some of electrodes 40C are configured to have small irrigation apertures. The apertures typically have diameters in an approximate range 0.1-0.2 mm. In the embodiment described herein cup electrode 40, ring electrode 42, and bump electrode 44 have respective sets of irrigation apertures 86, 88, and 90. The irrigation fluid for the apertures is supplied by irrigation module 52, which uses tubing 92 to transfer the fluid to the sets of irrigation apertures.

The irrigation fluid is typically normal saline solution, and the rate of flow of the fluid, controlled by module 52, is typically in the range of approximately 10-20 cc/minute, but may be higher or lower than this range.

Tubing 92 is routed to the electrodes by arranging it to pass through central opening 68 and to traverse central space 61 of member 60. By passing tubing 92 through the opening so as to traverse the central space of the coupling member the tubing makes no extra demands on the dimensional requirements, particularly the diameter, of the distal end, other than those required for force sensor 58. In some embodiments, the tubing may also be routed to pass through one or more of coils 76, 78, 80, and 82, further increasing the efficiency of the use of space within the distal end.

In order to supply each of electrodes 40C, tubing 92 connects to irrigation tubes 94, 96, and 98, which feed the irrigation apertures in respective electrodes 40, 42, and 44.

In some embodiments, valves, which are operated by controller 30 using irrigation module 52, are placed on at least one of tubes 94, 96, and 98, allowing the controller to set and/or switch the rate of flow of the irrigation fluid to the individual tubes. By way of example, tubes 94, 96, and 98 are assumed to have the irrigation flow through the tubes controlled by respective valves 100, 102, and 104. As is illustrated in FIG. 2, typically at least some of tubes 94, 96, and 98, and valves 100, 102, and 104, are located within central space 61.

Using the valves, controller 30 may set the rate of flow to the individual electrodes according to the function performed by the electrode. For example, if an electrode is being used for ablation, controller 30 may increase the flow rate through the electrode compared to when the electrode is not being used for ablation. Alternatively or additionally, controller 30 may alter the flow rate to a particular electrode according to a value of a parameter measured by a sensor in the distal end. Such parameters include the magnitude of the force measured by force sensor 58, as well as the direction of the force measured by the force sensor. Other sensors that the controller may use to alter the flow rate include a temperature sensor in the distal end.

Typically, controller 30 and irrigation module 52 maintain a minimum rate of flow of irrigation fluid through each of tubes 94, 96, and 98 and their respective electrodes, to prevent blood entering the tubes, the tubing, and the irrigation apertures of the electrodes.

In some embodiments, rather than having irrigation fluid supplied to the separate electrodes by via common tubing 92, which then connects to separate tubes for each electrode, separate irrigation tubes to each electrode are run from module 52 through probe 14. As with tubes 94, 96, and 98, controller 30 is able to adjust the irrigation flow rate through each of the separate tubes.

Figure 3:
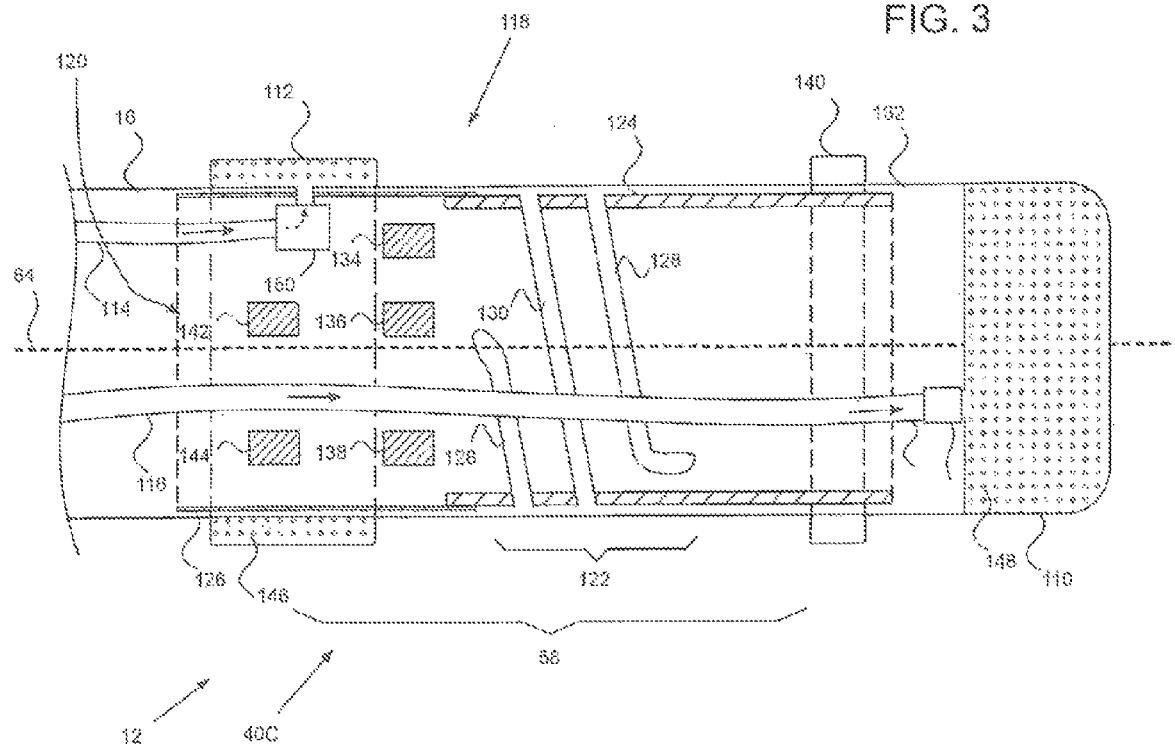
FIG. 3 is a schematic cross-section of a distal end of a catheter probe used in the system having dedicated irrigation tubes, according to an embodiment of the present invention.

An example of such an embodiment is illustrated in FIG. 3 which features electrodes 40C in the form of cup electrode 110 and ring electrode 112 that are fed by dedicated irrigation tubes 114 and 116, respectively. As with the embodiment shown in FIG. 2, distal end 12 is connected to insertion tube 16. The distal end has mounted upon it electrodes 40C, and force sensor 58 is mounted within the distal end. Shown schematically in section, force sensor 58 comprises a resilient tubular coupling member 118 having a central opening 120, which forms a spring joint 122 between two ends of the coupling member. As described above, coupling member 118 may be formed from a first part 124 and a second part 126 fixedly joined together. Similarly, coupling member 118 may be formed of a superelastic alloy.

Coupling member 118 may have a double helix including a first cut helix 128 and a second cut helix 130 in a portion of the length of first part 124 of the member, so that the member behaves as a spring. Coupling member 118 may be mounted within and covered by sheath 132, which is typically formed from flexible plastic material.

Within force sensor 58, a joint sensing assembly, comprising receiving coils 134, 136 and 138 and transmitting coil 140, provides accurate reading of any dimensional change in joint 122 as described above. This embodiment also features elliptical coils 142 and 144 configured to sense an externally applied field to facilitate positioning distal end 12 at a desired location within subject 22. Receiving coils 134, 136 and 138 may be located within one axial plane as described above and elliptical coils 142 and 144 in another. These coils may be used in conjunction with force module 48 and/or tracking module 54 as previously described.

As shown, electrodes 40C may have sets of irrigation apertures 146 and 148 for cup electrode 110 and ring electrode 112, respectively. First tubing 114 is routed to cup electrode 110 by arranging it to pass through central opening 68 in the manner previously described. Second tubing 116 is routed to ring electrode 112 by passing through central opening 68 and interfacing with flow diverter 150 which is configured to redirect irrigation fluid from a primarily axial direction to a primarily radial direction. Tubing 114 and 116 may be independently fed irrigation fluid by controller 30 using irrigation module 52 to provide separate control of flow rates to cup electrode 110 and ring electrode 112 to achieve the functionality noted above.

In this embodiment, flow diverter 150 may be positioned within or near the axial plane of elliptical coils 142 and 144. For example, flow diverter 150 and elliptical coils 142 and 144 may be spaced radially about catheter axis 84 at different azimuthal angles. This configuration allows flow diverter 150, and therefore, ring electrode 112 to be positioned relatively distally without interfering with the functionality of force sensor 58. It may be desirable to reduce the distance between cup electrode 110 and ring electrode 112 to provide efficient ablation of the tissue between the electrodes. At the same time, it may also be desirable to position ring electrode 112 proximal to spring joint 122 so as to reduce the distance between cup electrode 110 and force sensor 58, so that force sensor 58 may provide more accurate indication of the position of cup electrode 110.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A probe, comprising:
an insertion tube;
a distal electrode mounted on a distal end of the insertion tube;
a force sensor mounted in the distal end, the force sensor having a joint and a central opening and being configured to measure a force on the distal end;
a proximal electrode mounted proximal to the joint of the force sensor;
first tubing, running from a proximal end of the insertion tube to the distal end, passing through the central opening, and configured to supply irrigation fluid through apertures in the distal electrode; and
second tubing, running from a proximal end of the insertion tube, entering the central opening, and configured to supply irrigation fluid through apertures in the proximal electrode.

2. The probe according to claim 1, and comprising a controller configured to implement respective flow rates of the irrigation fluid to the respective sets of apertures.

3. The probe according to claim 2, wherein the controller is configured to set at least one of the respective flow rates in response to the force on the distal end.

4. The probe according to claim 1, wherein the force sensor has a tubular form enclosing a central space, wherein the first tubing traverses the central space and wherein the second tubing enters the central space.

5. The probe according to claim 4, further comprising a flow diverter positioned within the central space of the force sensor, wherein the flow diverter is in fluid communication with the second tubing.

6. The probe according to claim 4, wherein the flow diverter is configured to redirect irrigation fluid from a primarily axial direction to a primarily radial direction to feed apertures in the proximal electrode.

7. The probe according to claim 5, wherein the force sensor comprises at least one coil, and wherein the flow diverter is positioned in substantially the same axial plane as the at least one coil.

8. A method, comprising:
providing an insertion tube;
mounting a distal electrode on a distal end of the insertion tube;
mounting a force sensor in the distal end, the force sensor having a central opening and a joint, and being configured to measure a force on the distal end;
mounting a proximal electrode proximal to the joint of the force sensor;
passing first tubing running from a proximal end of the insertion tube through the central opening, the first tubing being configured to supply irrigation fluid through apertures in the distal electrode; and
passing second tubing, running from the proximal end of the insertion tube and entering the central opening, the second tubing configured to supply irrigation fluid through apertures in the proximal electrode.

9. The method according to claim 8, and comprising implementing respective flow rates of the irrigation fluid to the first and second tubing.

10. The method according to claim 9, and comprising setting at least one of the respective flow rates in response to the force on the distal end.

11. The method according to claim 8, wherein the force sensor has a tubular form enclosing a central space, and wherein the first tubing traverses the central space and wherein the second tubing enters the central space.

12. The method according to claim 11, further comprising directing irrigation fluid from the second tubing through a flow diverter positioned within the central space of the force sensor, wherein the flow diverter is in fluid communication with the second tubing.

13. The method according to claim 12, further comprising redirecting irrigation fluid from a primarily axial direction to a primarily radial direction to feed apertures in the proximal electrode with the flow diverter.

14. The method according to claim 12, wherein the force sensor comprises at least one coil, and wherein the first tubing is routed through the at least one coil and wherein the flow diverter is positioned in substantially the same axial plane as the at least one coil.

* * * * *